(12) United States Patent
Schon et al.

(10) Patent No.: US 8,317,799 B2
(45) Date of Patent: Nov. 27, 2012

(54) THERAPEUTIC MATERIAL DELIVERY SYSTEM FOR TISSUE VOIDS AND CANNULATED IMPLANTS

(75) Inventors: Lew C. Schon, Baltimore, MD (US); Richard H. Spedden, Clarksville, MD (US); Laura J. Pingel, Ellicott City, MD (US)

(73) Assignee: Bioactive Surgical, Inc., Clarksville, MD (US)

( * ) Notice: Subject to any disclaimer, the term of this patent is extended or adjusted under 35 U.S.C. 154(b) by 667 days.

(21) Appl. No.: 12/414,194

(22) Filed: Mar. 30, 2009

(65) Prior Publication Data
US 2010/0125240 A1 May 20, 2010

Related U.S. Application Data

(60) Provisional application No. 61/116,465, filed on Nov. 20, 2008, provisional application No. 61/154,718, filed on Feb. 23, 2009.

(51) Int. Cl.
*A61B 17/58* (2006.01)
*A61B 17/60* (2006.01)
*A61F 2/00* (2006.01)

(52) U.S. Cl. .......................................... 606/92; 606/94
(58) Field of Classification Search .............. 606/92–95, 606/304, 99, 104
See application file for complete search history.

(56) References Cited

U.S. PATENT DOCUMENTS

| | | | |
|---|---|---|---|
| 5,681,289 A | 10/1997 | Wilcox et al. | |
| 5,868,697 A | 2/1999 | Richter et al. | |
| 5,871,484 A | 2/1999 | Spievack et al. | |
| 6,019,761 A | 2/2000 | Gustillo | |
| 6,210,376 B1 | 4/2001 | Grayson | |
| 6,530,896 B1 | 3/2003 | Elliott | |
| 7,235,107 B2 | 6/2007 | Evans et al. | |
| 7,354,442 B2 | 4/2008 | Sasso et al. | |
| 2005/0015061 A1 | 1/2005 | Sweeney | |
| 2006/0184246 A1 | 8/2006 | Zwirkoski | |
| 2006/0241593 A1 | 10/2006 | Sherman et al. | |
| 2006/0246103 A1 | 11/2006 | Ralph et al. | |
| 2007/0010827 A1* | 1/2007 | Tu et al. | 606/108 |
| 2007/0162024 A1 | 7/2007 | Siemonsmeier | |
| 2008/0033572 A1 | 2/2008 | D'Antonio et al. | |

* cited by examiner

*Primary Examiner* — Andrew Yang
*Assistant Examiner* — Olivia C Chang
(74) *Attorney, Agent, or Firm* — Chalin A. Smith; Smith Patent Consulting

(57) ABSTRACT

Described herein is a novel drug delivery assembly having particular applicability to the field of orthopedic and surgical medicine. The devices and assemblies described herein enable the efficient application and retention of potentially expensive therapeutic materials to very specific locations, particularly those associated with voids in bone and tissue. One particularly unique aspect of the present invention involves the introduction of constructs which promote the retention of therapeutic material in the target area of application for beneficial use, for example by forming a proximal barrier that prevents leakage of the therapeutic material out of the target area. Additionally, the present invention provides unique devices and methods for surgical introduction of such constructs. The present invention finds particular application in connection with introduction of stem and progenitor cells, bioactive molecules and bone scaffold materials in conjunction with bone voids and with the use of cannulated implants, such as bone screws (also surgical screws) and pins. The present invention also has beneficial use in the delivery of cancer drugs, antimicrobials, bone cements and other therapeutic materials.

46 Claims, 5 Drawing Sheets

THERAPEUTIC MATERIAL DELIVERY SYSTEM FOR TISSUE VOIDS AND CANNULATED IMPLANTS

PRIORITY

The instant disclosure extends concepts enumerated in and claims priority to U.S. Provisional Application Ser. Nos. 61/116,465, filed Nov. 20, 2008, and 61/154,718, filed Feb. 23, 2009, the entire contents of which hereby are incorporated by reference herein.

FIELD OF THE INVENTION

The present invention relates to drug delivery, particularly in the field of orthopedic and surgical medicine. More particularly, the invention relates to devices and assemblies that enable the efficient application and retention of potentially expensive therapeutic materials to very specific locations, particularly those associated with voids in bone and tissue.

One particularly unique aspect of the present invention involves the introduction of constructs which promote the retention of therapeutic material in the target area of application for beneficial use, for example by forming a proximal barrier that prevents leakage of the therapeutic material out of the target area. Additionally, the present invention provides unique devices and methods for surgical introduction of such constructs.

The present invention finds particular application in connection with introduction of stem and progenitor cells, bioactive molecules and bone scaffold materials in conjunction with bone voids and with the use of cannulated implants, such as bone screws (also surgical screws) and pins. The present invention also has beneficial use in the delivery of cancer drugs, antimicrobials, bone cements and other therapeutic materials.

BACKGROUND OF THE INVENTION

Many orthopedic surgical procedures require the introduction of therapeutic, remedial or other beneficial material into or through holes created in the bone as part of the surgical process, whether by drilling, use of a coring device, use of a self-drilling screw or use of other mechanism. Bone or cartilage penetrations may be formed through the use of trocars and drills as a point of entry for many surgical procedures, including the introduction of liquid or paste type therapeutics and cements. In this context, cannulated screws and pins are used extensively to join tissues to bone and cartilage or connect sections of bone and/or cartilage. In many cases where holes are formed in bone, there is an advantage in providing a plug or seal in the hole or implanted cannulated device to assure retention of the therapeutic material in the desired area of effect.

Growth factors, bioactive molecules, stem and progenitor cells and other therapeutically beneficial material introduced into a damaged or diseased bone or at a bone-tissue junction through natural, disease-associated, or surgically induced holes or through cannulated implants can speed the healing process and/or address an underlying osteopathology (such as bone disease or bone cancer). Bone cements and other remedial materials can also be introduced through such natural or surgical penetrations, for example to correct a non-union deficiency or to fill voids created by failure of bone structure following previous surgery. Often antibiotics are introduced to correct or prevent infection. Chemotherapy agents can also be introduced to combat cancerous growth. Chemicals to permit detection of voids using conventional radiographic or other techniques also can be introduced through surgical holes or cannulated implants.

Problematic issues associated with the accurate and efficient placement of such therapeutic, remedial or other beneficial material at a specific points in a surgical penetration, such as one bridging the juncture of two bone sections, include, for example:

1. In those cases where the therapeutic material is injected through a hypodermic needle, difficulty can arise from the fact that confirmation of the needle tip location relative the juncture point is not easily available. In the case of minimally invasive techniques, the depth of soft tissue over the bone varies between patients and body areas and can actually fluctuate during surgery because of soft tissue swelling. Consequently, the depth of needle penetration in the bone itself may not be readily apparent, and use of radiological or other imaging means to confirm placement requires expensive equipment and is time consuming. Further, needle penetration into a bone screw or other device which is opaque to imaging technologies must be inferred rather that directly observed, which introduces an element of potential error.
2. Injected therapeutic material tends to rapidly flow out of the desired zone of application, particularly in the proximal direction (away from the target site), most often though the very hole created in the bone for the surgical procedure.
3. The therapeutic material may need to be introduced under pressure to successfully penetrate the surrounding tissue of interest, and an open hole does not support this pressurization.

Cannulated surgical screws are conventional in surgical procedures, particularly in the context of orthopedic surgery. The current state of the art provides for the injection of therapeutic materials into the bore of said screws, such that said material can potentially migrate to the distal end or tip of the screw and into the tissue there for therapeutic effect. In addition, fenestrated screws, provided with generally laterally disposed pores or "fenestrations", have been proposed to permit material introduction in areas around the screw threads or at the discontinuity of tissue, usually bone sections, being joined. However, since cannulated screws are open at both ends, there is the potential for the expensive therapeutic material being introduced to flow out either end of the screw, rather than through the fenestrations, as desired.

To address the issue of leakage, specially designed screws with integral valves have been proposed to prevent flow out of the proximal end or "head" of a bone screw; however, these type devices have the disadvantages of being overly specialized for a particular application. In addition, they are in many cases not compatible with the standard hex head driver tools available in many operating rooms. Caps which can be placed on the head of a screw have also been proposed. However, these also interfere with the driving of the screw or need to be installed after the screw is in place, potentially requiring unobstructed access to the screw head, which is not always possible. Additionally, cannulated surgical screws are often directed to the point of application by sliding the screw over a guidewire which has been inserted in or through the bone. The guidewire makes the pre-placement of a flow restriction in a screw prior to screw placement problematic.

Thus, there remains a need in the art, particularly in the case of cannulated surgical screws, for a generally applicable device and method that provides for efficient and restricted delivery and retention of therapeutic materials to a target location associated with a tissue void, preferably one that is readily adaptable for use with other surgical and interventional instruments that standard and conventional in the art.

SUMMARY OF THE INVENTION

In view of the aforementioned need in the art, the present invention provides devices and assemblies uniquely characterized for the delivery and retention of therapeutic material into bone, cartilage and similar tissues or through those tissues into other tissue. The novelty of the present invention is based not only its unique configurations, but also on the interaction between its parts, where each component provides multiple functions that combine to provide a functionality not available in current art.

Central to the instant invention is the provision of a plug suited for insertion into a tissue or implant device, such as a bone screw, and capable of impeding flow of the therapeutic material in the proximal direction, across the plug once implanted. In this manner, the plug of the present invention promotes the retention of the beneficial material in the region of desired effect. In addition to serving as a proximal barrier to flow, the plug of the present invention is preferably also itself a means for delivering therapeutic, remedial or other beneficial material. For example, it may be fabricated from a porous, viscous or gel-like material that is capable of retaining and dispensing over time beneficial therapeutic materials, such as growth factors, stem cells, antibiotics and the like. Particulars regarding the preferred materials for plug construction as well as the preferred therapeutic materials are discussed in greater detail below.

To achieve the desired effects, the present invention also contemplates the use of a core device comprising an injection port, such as a hypodermic needle or similar fluid delivery cannula, wherein a portion of the length of the needle is surrounded by, or adjacent to, the plug, further wherein the length of needle and plug are contained and constrained in a radial direction in a delivery tube or "plug guide", for example a cannula. Positioned on the proximal side of the plug within said plug guide is a plunger device, or "plug pusher", wherein the hypodermic needle passes along the linear axis of the plug pusher such that therapeutic material can be delivered by a syringe or other reservoir system from the proximal side of the plug pusher, through and to the distal side of the plug. Further, the radial orientation of the plug with respect to the hypodermic needle may be established prior the surgical procedure, for example as a pre-packaged assembly. In this manner, one may avoid the awkward and cumbersome task of coordinating the plug, plunger, and needle in the midst of the procedure, i.e., during or subsequent to the insertion of the plug into the tissue of the implant device, and thereby obviate the need for the needle to have to establish a channel through the plug after it has been inserted The plug is of a nature where, once in the target location (e.g., a bone cavity or hole), it can expand or otherwise deform (or expand) to create a flow restriction within the cavity; alternately, the plug can deform the cavity to achieve the same end (i.e., a full or partial hydraulic barrier that impedes fluid flow). The hypodermic needle can then be used to inject therapeutic material into the now isolated area of the void in tissue on the distal side of the plug. In one embodiment, the plug is fabricated from a self-sealing material capable of expanding or otherwise deforming to seal the needle path. Alternatively, the surrounding tissue can itself contract or deform to form the requisite fluid seal. In either case, the hypodermic needle can then be removed while the plug remains in place, acting in conjunction with the surrounding tissue to seal the needle path. It is further an aspect of the present invention that the plug pusher can be maintained in a position which secures the plug in place in the tissue or implant device while the needle is being removed, thereby eliminating the potential for the plug position to be altered appreciably by interaction with the needle as it is being removed.

To ensure proper position and stabilization, present invention contemplates a plug and plug pusher designed such that the linear axis shear force necessary to displace the plug once it is inserted into tissue or implant device is greater than the sum of the hydraulic force acting on the distal side of the plug and the tension force between the proximal end of the plug and the distal end of the plug pusher. This can be achieved through any or all of the following mechanisms: (i) utilizing a plug which expands once in place to create a radial force which increases the friction force between plug and cavity wall to a sufficient degree, (ii) utilizing adhesive materials in the plug design to provide a degree of bonding between the plug and the tissue or implant device, (iii) designing at least a portion of the plug as a flexible tube with a closed proximal end whereby an increase in hydraulic pressure increases the radial force of the tube against the surrounding wall, and further fabricating at least a distal end of the plug pusher and a proximal end of the plug from materials having low bonding potential. It is an object of the present invention to employ any and all of such optional mechanisms.

As noted above, the present invention contemplates the use of the plug and core device in conjunction with a delivery tube or plug guide, such as a cannula. The diameter or geometric configuration of the distal end of the plug guide, which engages the proximal end or entrance to the tissue, bone screw or other implant device is such that it establishes a predetermined linear axis relationship between the distal end of the plug guide and the proximal side/end of the tissue or implant; essentially, the plug guide provides a positive stop to set the relative position of the assembly of the present invention and the bone. Accordingly, it is an aspect of the present invention that the relative linear dimensions of the hypodermic needle (or flow tube or core device), plug guide (or cannula or delivery channel) and plug pusher (or plunger) are such that when used together, (a) the distal end or tip of the needle is deployed at a predetermined depth in the tissue or an implant device, such as a bone screw, (b) the plug is inserted at a predetermined depth, and (c) the relationship of the tip of the needle and the distal end of the plug are predetermined and allow for free passage of therapeutic material to the distal side of the plug.

Additionally, the process of inserting the needle and plug into the tissue or implant device should not appreciably change the desired relative orientation of the needle and plug, which might otherwise be the case if an attempt was made to push the needle through a plug which had been pre-positioned in the bone. The present invention further contemplates the inclusion of a mechanism for coordinating the axial displacement the needle (or flow tube) with the axial displacement of the plug material into the target tissue. Such coordination may result from positioning, force transmitting contact, linkage or other mechanism. In a preferred embodiment, the mechanism for coordination can arise through contact between the flow tube and the plug pusher; in the case where the flow tube is a hypodermic needle, the contact can be between the proximal side (needle side) of the needle fitting head (such as a luer-lock fitting head) and the distal surface of the plug pusher, such that force imparted on the distal side of the needle is transmitted to the plug pusher as well. In other embodiments, a removable device, such as a stop pin or clip, may be used to temporarily secure the flow tube to the plug pusher in a manner which ensures coordinated axial movement of the two. The stop pin or clip can then be removed prior to extracting the flow tube from the plug.

In a preferred embodiment, the plug guide cannula of the present invention is dimensioned such that the inside diameter of its distal end is approximately equal to or less than the inside diameter of the bore of the bone screw, other implant device or hole in the tissue. In this manner, the plug retained therein can be pushed from the plug guide and into the bore with minimal of disruption of the plug. Additionally, the distal end of the plug pusher, which abuts the proximal side of the plug, may be displaced through the plug guide cannula to a point approximately flush with the plane of the juncture of the plug guide cannula and the opening into the tissue void or bore of the implant device. Alternatively, the distal end of the plug pusher may extend a predetermined distance into the tissue or implant device to ensure secure deployment of the plug.

In another preferred embodiment, the present invention provides the plug guide cannula having a decreasing cross-sectional area, tapering towards its distal end in a manner which compresses the plug just prior to the plug being introduced into the tissue or implant device.

In yet another preferred embodiment of the present invention, the outside diameter of the plug guide cannula, at or near its distal end, is sufficient to prohibit, or limit the depth of insertion of the plug guide cannula into the bone screw, other implant device or hole in the tissue. In the case of a bone screw, the distal end of the plug guide, or a point along the linear axis near the distal end, can preferably be of a diameter or configuration to fit inside the head of the bone screw, but not into the inner bore of the body of the screw. Typically bone screws have a hex driver compatible head. Accordingly, it may be preferable in certain embodiments to provide the distal end of the plug guide with a hex configuration.

In another preferred embodiment of the present invention, the plug guide is dimensioned such that the inside diameter of its distal end is greater than the inside diameter of the bore of the bone screw, other implant device or tissue opening. In this embodiment, the distal end of the plug may be of a diameter less than the inside diameter of the bore in the tissue or implant, and the proximal end of the plug may be of a diameter greater than the inside diameter of the bore or hole. In this manner the plug will have an interference fit with the bore or hole, a fitting that is analogous to a stopper or cork in a bottle.

It is also an object of the present invention to provide a visual indication of the depth of plug and needle insertion in the tissue or the bone screw or other implant device embedded in the tissue. In the present invention, this information can be extrapolated from the relative positions of the plug pusher and the plug guide cannula. To that end, it may be desirable to provide the shaft of the plug pusher with one or more mark along the linear axis, the visualization of such marks (or lack thereof, when covered by the plug guide cannula) serving as indicia of the depth to which the plug pusher (or plunger) is displaced into the plug guide cannula.

It is also an object of the present invention to permit the devices and assemblies of the present invention to be utilized to extract fluid material from a tissue void or a cannulated implant device. In such a system, the hypodermic needle would be connected to a reservoir or drain system external to the body where the hydraulic pressure was sufficiently less than that at the tip of the needle in the tissue void or implant.

It is also an object of the present invention to utilize two or more of pre-fabricated devices or assemblies constructed in accordance with the present invention in conjunction with each other, wherein the devices are implanted into tissue voids or implants which access a common hydraulically linked system in the body, such that fluid may be injected into one device and pressure can be relieved or fluid extracted from the second device. In such a manner, the devices can be used to vent gases, replace fluids or be used in a flow through system as might be appropriate for flushing materials or fluids from an area of tissue.

The present invention also contemplates the use of one or more hypodermic needles or flow tubes in conjunction with a single plug. These multiple needles can be used to inject different therapeutic materials or two components that interact when mixed. In this context, one needle can be appreciably longer than the other and one can be used to inject material while the other is used to extract material as might be envisioned in a fluid replacement system, a pressure venting system or a flushing system. The flushing capabilities of the present invention have particular value in the removal of diseased or excess fluid or gases which may be causing harm or which may impair the effectiveness of introduction of or function of the therapeutic molecules being introduced, or in circulating said fluids through bodily tissues.

To avoid interference with surrounding tissue, surgeons may use a large bore cannula (referred to here as a "third cannula") as a guide through which to insert trocars, drill bits, surgical wires or other devices for creating holes in bone or other tissue. The present invention contemplates the mating or insertion of a plug guide of the instant invention with such a third cannula to permit insertion of the plug/needle core assembly of the present invention in the hole in the bone. The lengths of the device components of the present invention can be predetermined in relationship to the length of the third cannula to provide the desired depth of penetration of the plug and needle tip. In some instances a surgeon will place a cannulated bone screw through said third cannula. Accordingly, it is an object of the present invention to fabricate the plug guide of the present invention with a length sufficient to pass through the third cannula and engage the proximal end or head of the screw.

It is yet another object of the present invention to provide for the inventive components as a pre-packaged and/or sterile assembly, such an assembly including a hypodermic needle or core device, a plug, a plug guide or cannula and a plug pusher or plunger. Alternatively, the assembly components (e.g., a flow tube such as a hypodermic needle, a plug, a plug guide cannula and a plug pusher or plunger) may be separately supplied and packaged for on site assemblage before or during surgery.

The present invention also provides a surgical method of use comprising the steps of (a) inserting a hypodermic needle and plug as a single unit into a void in tissue or an implant device, (b) injecting a therapeutic material into the void on the distal side of the plug; and (c) removing the needle in a manner whereby the plug and therapeutic material remain in the tissue or implant device.

In accordance with the teachings of the present invention, the above-mentioned method of use may optionally include any or all of the following steps:
  (i) Forming the plug material in a geometric shape in a plug guide cannula with a hypodermic needle or other fluid portal transiting its length and with a plug pusher positioned at the proximal end of the cannula;
  (ii) Attaching a syringe or other reservoir with therapeutic materials at the proximal end of the hypodermic needle;
  (iii) Positioning the distal end of the plug guide cannula such that it is placed in or abuts a void in a tissue or a bore of a cannulated implant device in tissue;

(iv) Pushing the plug pusher into the plug guide cannula in a manner which displaces both the plug and the hypodermic needle into said void or bore;
(v) Injecting the therapeutic material through the hypodermic needle into the void or bore on the distal side of the plug;
(vi) Removing either the hypodermic needle from the plug and then the plug pusher/plug guide cannula assembly from contact with the tissue or implant device, or removing the flow tube/ plug pusher/ plug guide cannula as a single unit from contact with the tissue or implant device.

The present invention also contemplates:
(i) A hypodermic needle or flow tube in which an associated plug is inserted into tissue such that the distal end of the needle or flow tube is hydraulically attached to a void in the tissue and the proximal end of the needle or flow tube is attached to a reservoir or syringe containing a fluid to be injected into a tissue void, or 'source fluid'.
(ii) The use of a second hypodermic needle or flow tube in the same or another device of the present invention, inserted along with its associated plug into tissue such that the distal end of the flow tube is hydraulically attached to a void, which is also hydraulically attached to the void and the proximal end of the flow tube is attached to a receiver reservoir or a drain.
(iii) Manipulating the components of the system such that relative pressures in the system induce flow from the 'source fluid' reservoir into the void while fluid from the void flows to the receiver reservoir or drain. Typical this flow can be induced by pressurizing the source fluid reservoir, putting the receiver reservoir under relative vacuum or placing a flow inducing device, such as a pump, in the hydraulic system. The present invention thus contemplates that the source reservoir and receiver reservoir can be the same vessel, particularly if a flow inducing device is provided in a line to or from said reservoir.

The present invention also provides a surgical method of use comprising the steps of (a) inserting a hypodermic needle and plug as a single unit into a void in tissue or an implant device, (b) aspirating or removing material from the void on the distal side of the plug; and (c) removing the needle in a manner whereby the plug and therapeutic material remain in the tissue or implant device.

In accordance with the teachings of the present invention, the above-mentioned method of use may optionally include any or all of the following steps:
(a) Forming the plug material in a geometric shape in a plug guide cannula with a hypodermic needle or other fluid portal transiting its length and with a plug pusher positioned at the proximal end of the cannula;
(b) Positioning the distal end of the plug guide cannula such that it is placed in or abuts a void in a tissue or a bore of a cannulated implant device in tissue;
(c) Pushing the plug pusher into the plug guide cannula in a manner which displaces both the plug and the hypodermic needle into said void or bore;
(d) Aspirating or otherwise removing material through the hypodermic needle from the void or bore on the distal side of the plug; and optionally
(e) Removing either the hypodermic needle from the plug and then the plug pusher/plug guide cannula assembly from contact with the tissue or implant device, or removing the needle/ plug pusher/plug guide cannula as a single unit from contact with the tissue or implant device.

These and other objects and features of the invention will become more fully apparent when the following detailed description is read in conjunction with the accompanying figures and examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

Examples, drawings and descriptions, herein, may refer to specific tissue and/or implant device constructs where the device might be applied, such as cannulated bone screws; however, the devices, assemblies, and methods of the present invention are equally applicable to other situations, for use with any other medical implant devices having a fluid port or hollow core, as well as to holes in tissue, including those which are surgically induced or the result of defect disease or trauma. Additionally, examples, drawings and descriptions typically refer to human patients; however the constructs of this invention are equally applicable to other biological entities.

BRIEF DESCRIPTION OF THE DRAWINGS

Various aspects and applications of the present invention will become apparent to the skilled artisan upon consideration of the brief description of the figures and the detailed description of the present invention and its preferred embodiments which follows.

Hypodermic needle or other therapeutic material flow tube (1)
Plug Pusher and Needle Guide (2)
Plug (3)
Plug Guide Cannula (4)

Figure 1:
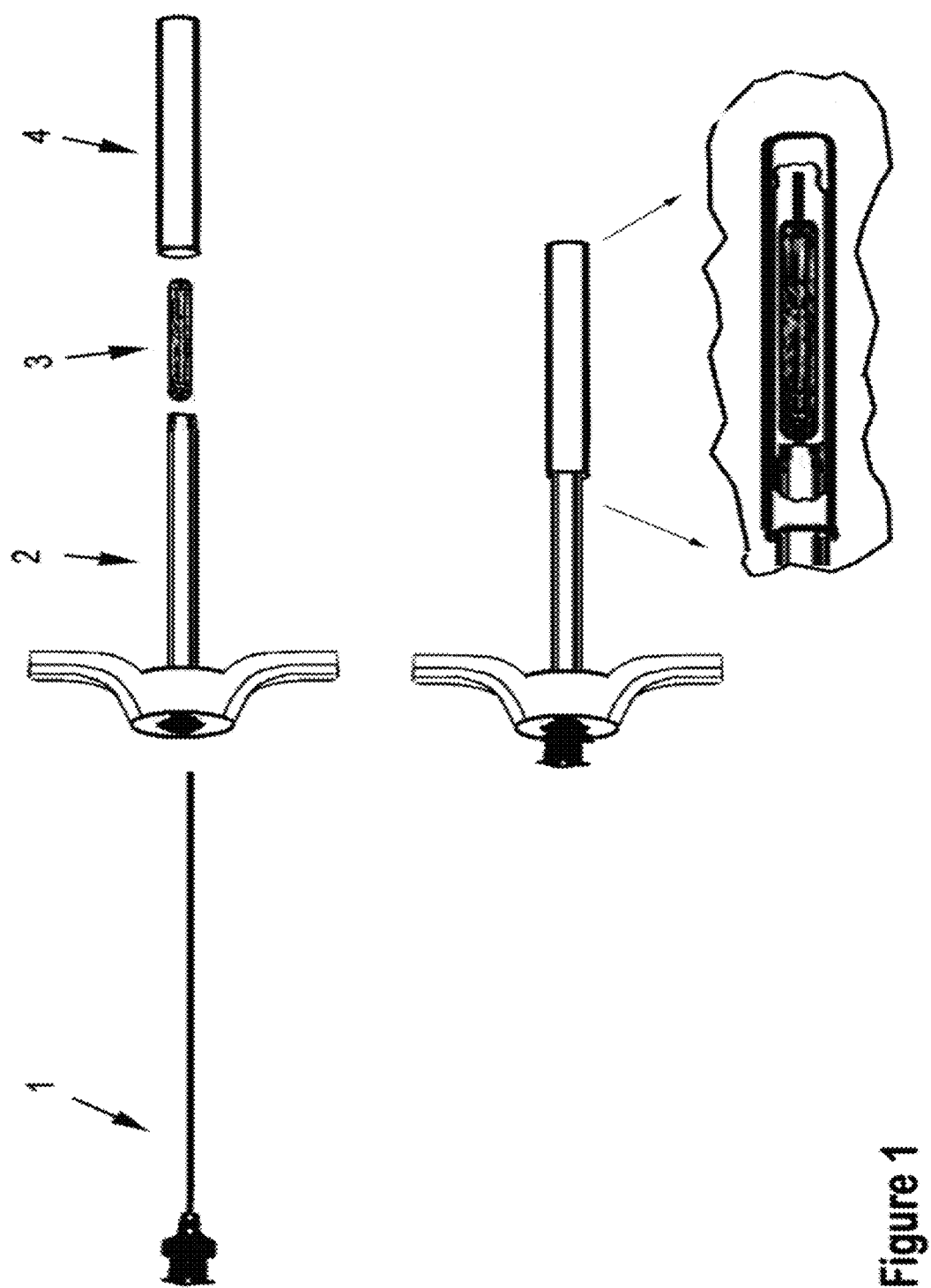
FIG. 1 depicts the components of the present invention as individual elements and as an assembled device as may be provided in a sterile package for use in surgery. The individual elements can vary in design as might be envisioned by one skilled in the art without modifying the purpose of the elements or the interaction between elements which is fundamental in the present invention. The elements of FIG. 1 include.

The cut-away view in FIG. 1 depicts the plug positioned in the plug guide, with the distal end of the plug pusher positioned such that motion of the plug pusher into the plug guide cannula will displace the plug towards and out of the distal end of the plug guide cannula.

Figure 2:
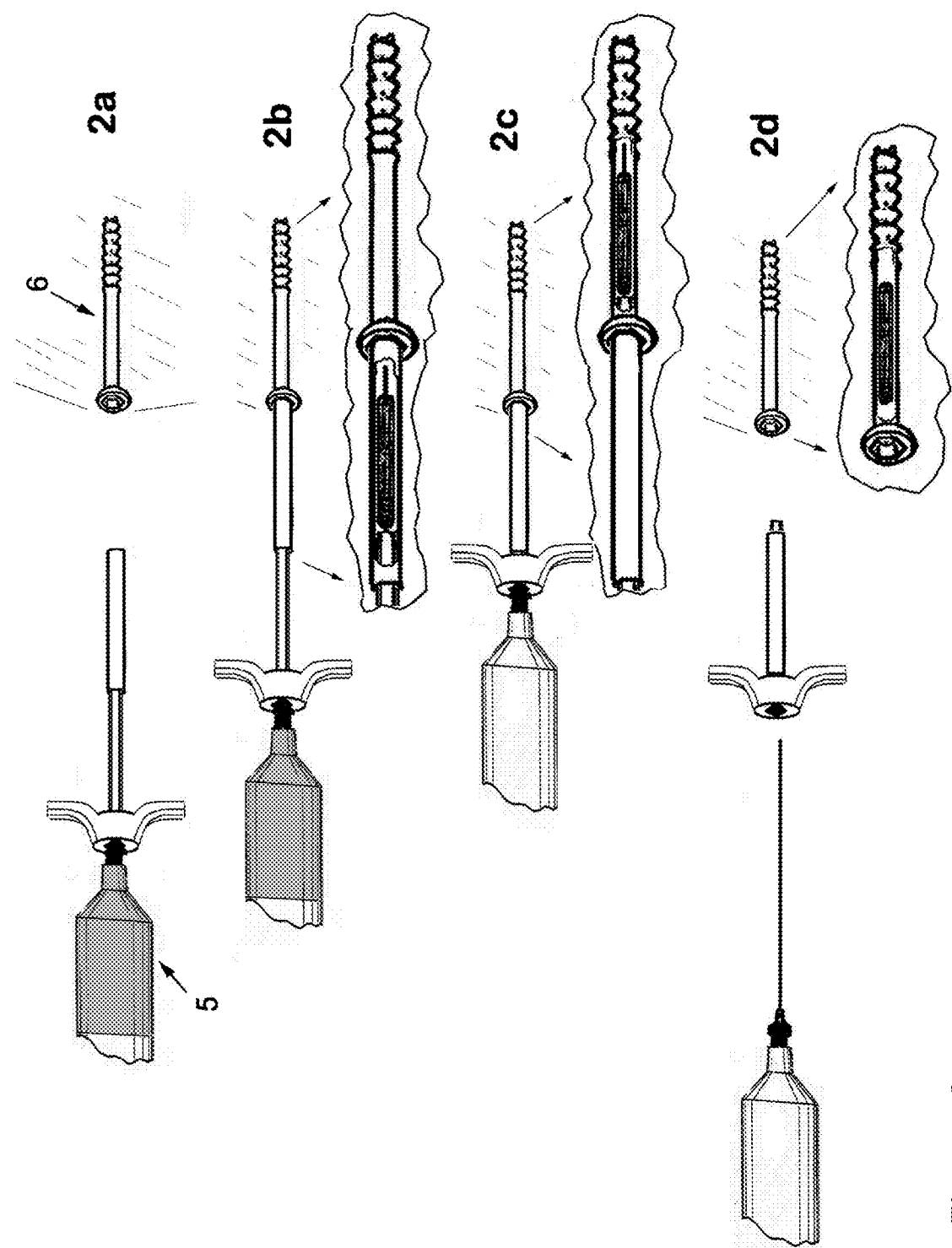

FIG. 2 depicts the sequence of use of the device. In Frame 2a, a syringe with therapeutic liquid is attached to the hypodermic needle of the device using a conventional luer-lock-type fitting, though other common attachment mechanisms are also contemplated. In this example, the target destination for the therapeutic fluid is the bore of a bone screw (6) embedded in bone. In Frame 2b, the distal end of the plug guide is inserted into the hex driver fitting in the proximal end of the bone screw. The outside diameter of the plug guide is less than or equal to the diameter of a circle drawn to the inside of the tangents of the faces of the hex. The inside diameter of the plug guide is approximately equal to or less than the diameter of the bore of the bone screw. Frame 2c depicts the position of the plug and needle inside the bone screw after, first, the plug pusher is pushed towards and into the plug guide, such that it completely displaces the plug to a predetermined depth in the bone screw, and second, the contents of the syringe are discharged through the needle into the bore of the bone screw on the distal end of the plug. It is important to note that because the plug pusher is forcing the plug to remain in position during the injection of the therapeutic material into the bone screw on the distal side of the plug, the therapeutic fluid can be injected using a large amount of pressure without danger of the plug blowing out of the proximal end of the bone screw. This is important in the function of the present invention, since bodily tissue can present initial resistance to the introduction of fluid, however once successfully introduced, the pressure normalizes to those more typically found in a body. Frame 2d depicts the plug remaining in the bone screw after the plug pusher/plug guide cannula and the syringe/hypodermic needle assemblies have been removed.

Figure 3:
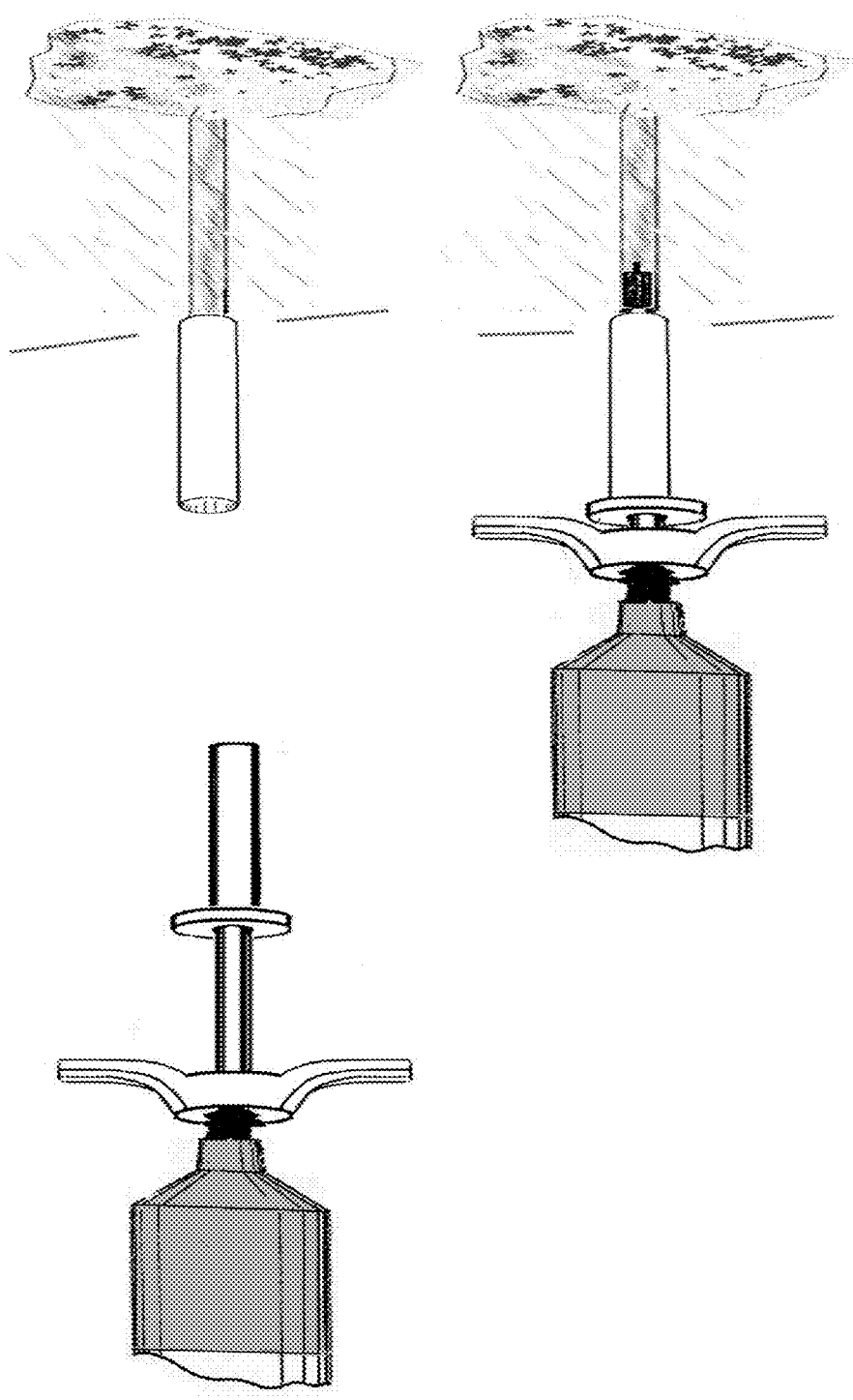

FIG. 3 depicts the device of the present invention in conjunction with a cannula (surgical cannula, also third cannula) such as might be present in a when a trocar/cannula system is used to create a hole in a bone, or wherein a cannula is used to guide a drill bit in forming a hole in bone. In this particular embodiment depicted, the plug guide cannula is shown with a limiting diameter on the proximal end, such that it engages the proximal end of the surgical cannula, and the length of the plug pusher and plug guide cannula are sufficient to allow the plug to be deposited within the bone. Alternately, in a situation where the surgical cannula is larger in diameter than the hole in bone, a plug guide cannula with an outside diameter which is less than the inside diameter of the surgical cannula, but greater than the diameter of the hole can be used to limited the degree of penetration of the plug guide cannula into the hole, and in such a case, the depicted enlargement at the proximal end of the plug guide cannula is not required to limit penetration into the tissue. This figure also depicts a situation where the hole in the bone is used to access a diseased, cancerous or necrotic area of bone.

Figure 4:
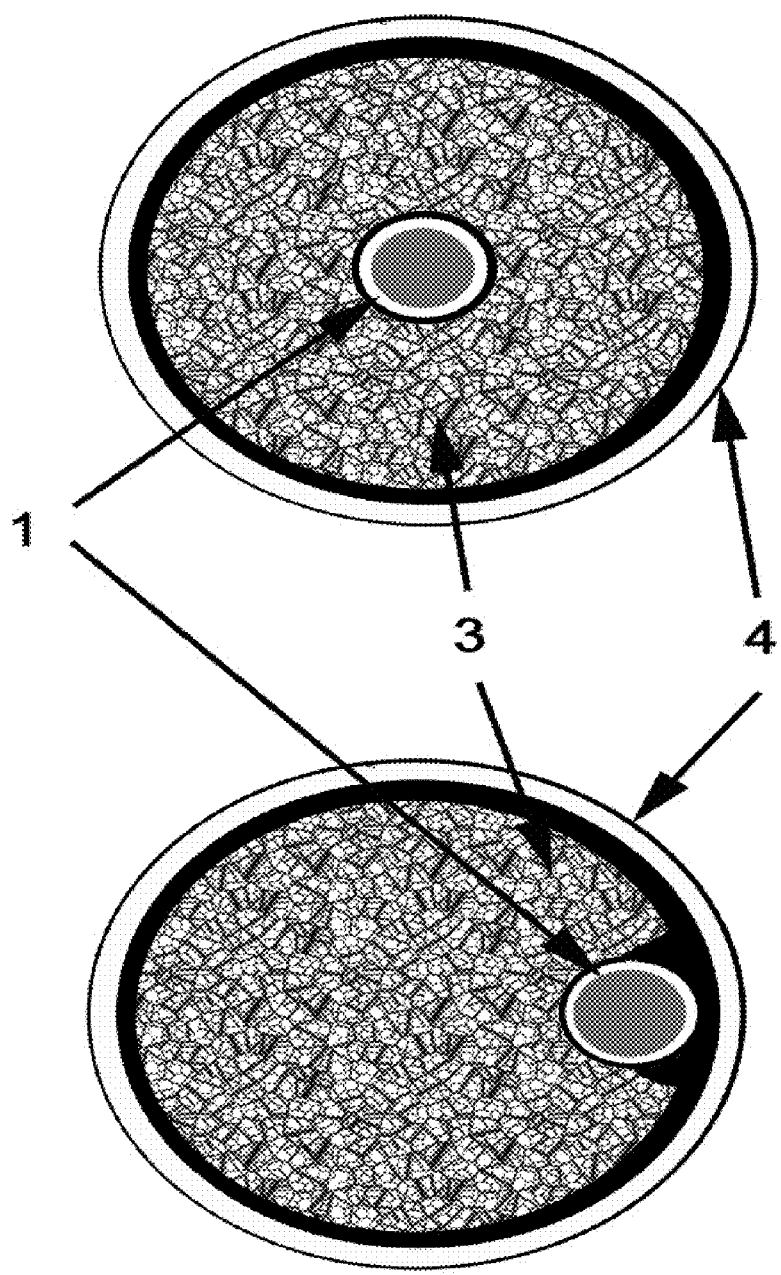

FIG. 4 is a cross-sectioned view depicting two potential orientations of the hypodermic needle (1) with respect to the plug guide cannula (4) and plug (3) to be deployed. In the top cross-section, the hypodermic needle is positioned approximately concentric with the plug. In the bottom cross-section, the needle is positioned eccentrically. An eccentrically positioned plug results in reduced drag between the plug and needle when the needle is removed; however there is more of a chance of interference between the needle and the wall of the hole in the tissue or bore of the implant device when the needle and plug are first inserted.

Figure 5:
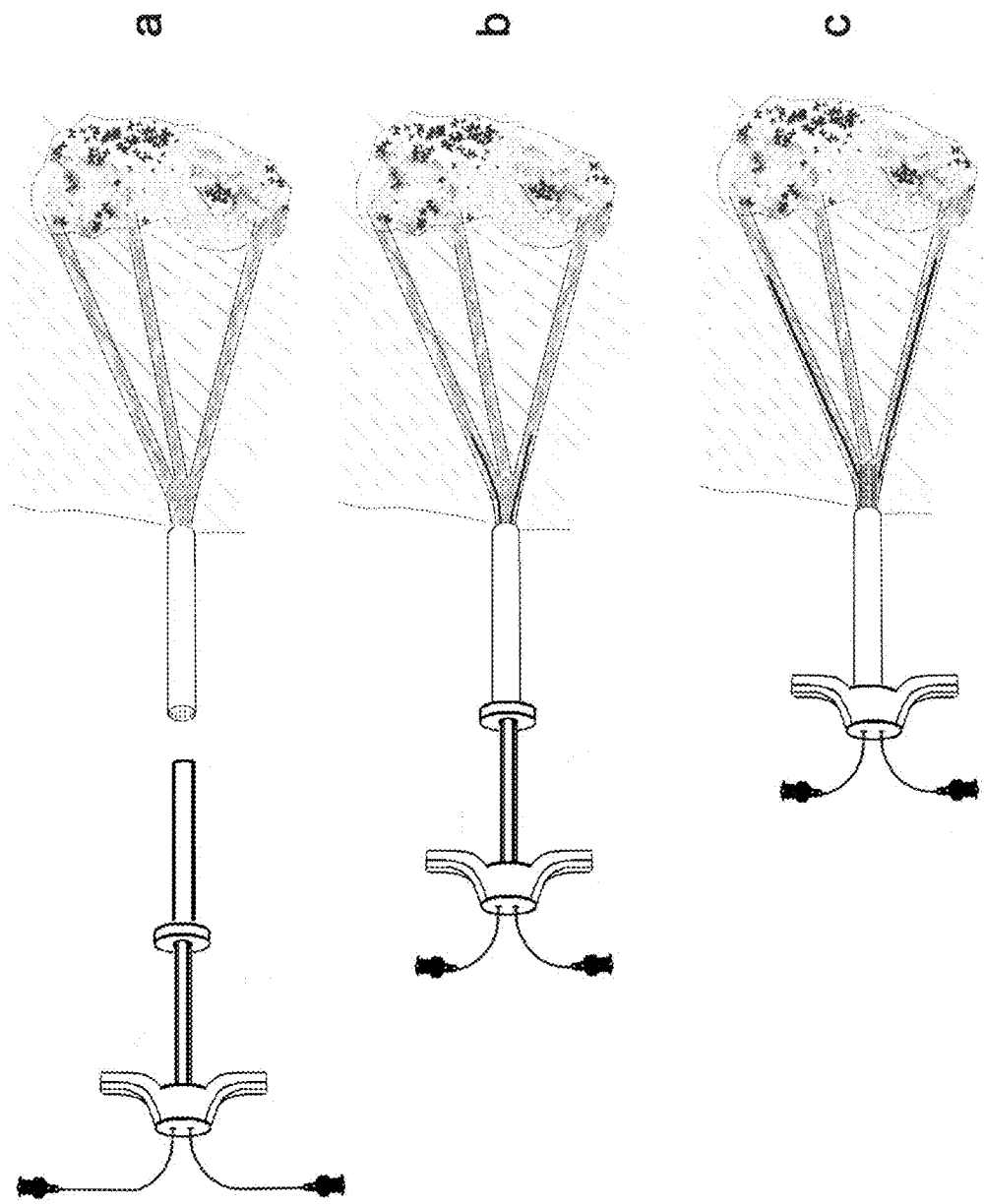

FIG. 5 depicts the use of flexible needles to access holes at different angles to the bone surface, as well as to deliver therapeutic material to a greater depth in a bone. This figure also depicts the establishment of a flushing configuration using a single device. In FIG. 5a, two flexible needles are provided in a device of the present invention suitable for use with a third cannula. The third cannula has been used as a drill guide for establishing holes to different portions of a hydraulically connected region of necrotic bone. In FIG. 5b, the device has been inserted into the third cannula, and by tilting the orientation of the third cannula to the bone, the needles are fed into first one hole and then the other, by pushing on the flexible needles and feeding them through the device and the plug. Once the needles are established in their respective holes, the plug pusher is depressed to displace the plug into the common entry hole and to displace the needles further into their respective holes, as depicted in FIG. 5c. At this point, a flush media reservoir can be attached to the connector on one needle and the other needle can be used to feed a drain or recovery reservoir. It should be noted that the needles access different parts of the necrotic tissue, maximizing the region flushed, and that the presence of the plug not only inhibits flow out of the bone, but also serves to inhibit flow between the holes (short cutting).

DETAILED DESCRIPTION OF THE PREFERRED EMBODIMENTS

The present constitutes a marked improvement in the area of injection of therapeutic materials into voids in tissue such as bone and/or implant devices such as bone screws, not only because it provides multiple functions in a single device, which both saves time and reduces the potential for error during surgery, but also because the interaction between the parts provides functionality not available if the components were implanted individually. Noted advantages include:

The plug material is maintained in a sleeve, namely the plug guide cannula, prior to and during implantation and may be pre-formed to be compatible with the standard trocar, drill bit, or bone screw bore sizes. This plug guide cannula, not only compresses the plug into the desired geometric configuration, but also serves as a channel and mating unit which engages the proximal opening to the void in the tissue or implant and guides the plug into such. Additionally, the plug guide cannula serves a protective purpose while the device is in the sterile package and during handling in surgery; in particular, the plug guide cannula protects against mechanical damage, and reduces exposure to open air which might result in excessive evaporation of liquid components of the plug or exposure to airborne contaminants.

The needle transits the length of the plug prior to insertion in the body tissue (or implanted device), and the needle and plug may be assembled and inserted as a unit. If the needle is inserted after the plug is inserted, there is the potential for the needle to either not completely transit the plug or push the plug further into the tissue than desired; plug material may also jam in the bore of the needle.

The device provides a positive means to set both the plug depth and the needle tip depth in the tissue.

The plug pusher holds the plug in place during the injection of therapeutic material, thereby allowing the surgeon to apply a force sufficient to overcome hydraulic resistance in the surrounding tissue, not only assuring delivery of the therapeutic, but also providing important tactile feedback to the surgeon. If the surgeon were just to inject through a plug, there is the potential for the plug to 'blow back'.

The plug pusher can hold the plug in place while the needle is being extracted;

otherwise friction between the needle and the plug might pull the plug part or all of the way out of the hole in the bone or bore of the screw.

Elements of the Present Invention:

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

Unless otherwise defined, all technical and scientific terms used herein have the same meaning as commonly understood by one of ordinary skill in the art to which the present invention belongs. However, in case of conflict, the present specification, including definitions, will control.

In the context of the present invention, the following definitions apply:

The words "a", "an" and "the" as used herein mean "at least one" unless otherwise specifically indicated. Thus, for example, reference to a "molecule" is a reference to one or more molecules and equivalents thereof known to those skilled in the art, and so forth.

The term "proximal" as used herein refers to that end or portion which is situated closest to the user of the device, farthest away from the target surgical site.

The term "distal" as used herein refers to that end or portion situated farthest away from the user of the device, closest to the target surgical site.

The term "axial" as used herein refers to the direction relating to or parallel with the longitudinal axis of the device. In the context of the present invention, the plug positioned within the bore of the plug guide cannula and may be axially (distally) moved therein and displaced therefrom by means of a plug pusher or plunger.

The term "lateral"" as used herein refers to the direction relating to the transverse axis of the device. In the context of the present invention, the target site may be provided with a fenestrated surgical screw having a series of pores or fenestrations positioned about its lateral surface.

The present invention is directed, at least in part, to the introduction and retention of therapeutic materials (also referred to herein as remedial, beneficial and/or therapeutic agents) through holes or voids in bodily tissue or through the bore of an implanted device. In the context of the present invention, the term "therapeutic", "therapeutic materials" and "remedial", "beneficial" and "therapeutic" "agents" refers to any material which is, or can be, injected through a hypodermic needle or other cannula device, into tissue with an intended effect which is advantageous to the health or well-being of the patient. Of particular value in the context of the present invention are those agents with known benefit to the musculoskeletal system, such as, stem and precursor cells and other biological cells, bioactive cytokines (particularly growth factors, bone morphogenetic protein, angiogenesis factors), hormones, adipose extracts, anti-cancer drugs (including chemo-therapy agents), bone cements and mixtures comprising in part calcium bearing molecules, antibiotics and other anti-infection agents, blood thinning agents, analgesics, DNA and combinations of any or all of the above. In the context of the present invention, bone marrow aspirate and compositions comprising such are of particular value.

In the context of the present invention, the term "stem cell" represents a generic group of undifferentiated cells that possess the capacity for self-renewal while retaining varying potentials to form differentiated cells and tissues. Stem cells can be totipotent, pluripotent or multipotent. Derivative stem cells that have lost the ability to differentiate also occur and are termed 'nullipotent' stem cells. A totipotent stem cell is a cell that has the ability to form all the cells and tissues that are found in an intact organism, including the extra-embryonic tissues (i.e. the placenta). Totipotent cells comprise the very early embryo (8 cells) and have the ability to form an intact organism. A pluripotent stem cell is a cell that has the ability to form all tissues found in an intact organism although the pluripotent stem cell cannot form an intact organism. A multipotent cell has a restricted ability to form differentiated cells and tissues. Typically adult stem cells are multipotent stem cells and are the precursor stem cells or lineage restricted stem cells that have the ability to form some cells or tissues and replenish senescing or damaged cells/tissues. Further information may be found in WO 08/007082, the contents of which are incorporated by reference herein.

In the context of the present invention, the term "progenitor cell" refers to unipotent or multipotent cells, which comprise the stage of cell differentiation between stem cells and fully differentiated cells.

In the context of the present invention, the term "biological cell" refers to any cell capable of performing useful biological functions in a living organism, particularly replication to form a tissue structure. The term as used herein includes stem cells, progenitor cells and fully differentiated cells. Biological cells may include cells from the intended host organism or those from a donor organism. Biological cells can include cells from recombinant or genetic engineering techniques.

In the context of the present invention, the term "bioactive molecules" refers to any molecule which has the capacity to interact with a living tissue or system in such a way as to exhibit or induce a biological activity in an organism, tissue, organ or cell, either in vivo, in vitro or ex vivo. The term "bioactive molecule" extends to precursor forms thereof. Precursor proteins, for example BMP precursors, are typically inactive until they undergo endoproteolytic cleavage; however, in that this is a process that naturally occurs in the body, the present invention extends to precursor proteins that participate in useful biological processes in the body.

Of particular interest in the context of the present invention are bioactive peptides that trigger or regulate biological functions. Illustrative examples of bioactive molecules suitable for use in the context of the present invention include, but are not limited to, are growth factor proteins, such as TGFβ, BMP-2, FGF and PDGF.

In the context of the present invention, the term "growth factors" refers to the broad class of bioactive polypeptides which controlling and regulating a variety of endogenous biological and cellular processes, such as cell-cycle progression, cell differentiation, reproductive function, development, motility, adhesion, neuronal growth, bone morphogenesis, wound healing, immune surveillance and cell apoptosis. Growth factors typically operate by binding to specific receptor sites on the surface of target cells. Growth factors include, but are not limited to, cytokines, chemokines, polypeptide hormones and the receptor-binding antagonists thereof. Examples of well known growth factors include but are not limited to:

Bone Morphogenic Protein (BMP);
Transforming growth factor beta (TGF-β);
Interleukin-17;
Transforming growth factor alpha (TGF-α);
Cartilage oligomeric matrix protein (COMP);
Cell Density Signaling Factor (CDS);
Connective tissue growth factor (CTGF);
Epidermal growth factor (EGF);
Erythropoietin (EPO);

Fibroblast growth factor (FGF);
Glial Derived Neurotrophic Factors (GDNF);
Granulocyte-colony stimulating factor (G-CSF);
Granulocyte-macrophage colony stimulating factor (GM-CSF);
Growth differentiation factor (GDF);
Myostatin (GDF-8);
Hepatocyte growth factor (HGF];
Insulin-like growth factor (IGF);
Macrophage inhibitory cytokine-1 (MIC-1);
Placenta growth factor (PlGF);
Platelet-derived growth factor (PDGF);
Thrombocyte concentrate (PRP);
Thrombopoietin (TPO);
Vascular endothelial growth factor (VEGF);
Activin and Inhibin;
Coagulogen;
Follitropin;
Gonadotropin and Lutropin;
Mullerian Inhibiting Substance (MIS) also called: Anti-Müllerian hormone (AMH) Mullerian inhibiting factor (MIF) and Mullerian inhibiting hormone (MIH);
Nodal and Lefty; and
Noggin Therapeutic molecules which regulate, induce or participate in useful biological processes in the body, including those listed above, are often categorized or classified according to their particular structure or function. For example, immunoregulatory proteins secreted by cells of the immune system, such as interleukin and interferon, are often referred to as cytokines. Other categories of regulatory molecules include, but are not limited to:

morphogens (e.g., molecules that regulate or control the formation and differentiation of tissues and organs);

chemokines (e.g., any of a group of cytokines produced by various cells, as at sites of inflammation, that stimulate chemotaxis in white blood cells such as neutrophils and T cells);

hormones (e.g., a product of living cells that circulates in body fluids such as blood and produces a specific, often stimulatory effect on the activity of cells, usually remote from its point of origin);

receptors (e.g., a molecule present on a cell surface or in the cell interior that has an affinity for a specific chemical entity, including both endogenous substances such as hormones and ligands as well as foreign materials, such as viral particles, that serves as an intermediary between the stimulating agent and the downstream physiological or pharmacological response thereto;

receptor-binding agonists (e.g., a chemical substance capable of combining with a specific receptor on a cell and initiating the same reaction or activity typically produced by the endogenous binding substance (such as a hormone); and receptor-binding antagonists (e.g., a chemical substance that reduces the physiological activity of another chemical substance (such as a hormone) by combining with and blocking one or more receptors associated therewith).

However, since the study of the function of the various regulating moieties in the body is still an emerging science, the categorization thereof is also evolving. Accordingly, the present invention is not limited to any one particular class or category of regulating or stimulating molecules.

As used herein, the term "growth factors" also refers to precursor forms of growth factors, which are typically inactive until they undergo endoproteolytic cleavage, as well as synthesized and recombinant forms which provide part or all of the same or similar functions as the naturally occurring growth factors. Accordingly, the present invention encompasses precursors, analogues, and functional equivalents of growth factors, provided the resulting molecules retain some or all of the function of regulating useful biological processes in the body, typically by binding to specific receptor sites on the surface of target cells associated with the wild-type or endogenous moiety.

The term "therapeutic agents" as used herein refers to any molecule, compound or composition having therapeutic potential, more particularly pharmaceutical activity. Examples of particularly useful therapeutic and/or pharmaceutical activities include but are not limited to anti-coagulation activity, anti-adhesive activity, anti-microbial activity, anti-proliferative activity, and biomimetic activity.

In the context of the present invention, the term "therapeutic materials" refers to any composition which comprises any of the following: therapeutic agents, bioactive molecules, stem cells, progenitor cells or biological cells. The term "bioactive solution" refers to a liquid composition which comprises, in part, bioactive materials.

In the context of the present invention, the term "antimicrobial" refers to any molecule which has the capacity to limit or interfere with the biological function of a bacterial, fungal or viral pathogen or a toxin. Antimicrobial is intended to also encompass antibacterial, antibiotics, antiseptics, disinfectants and combinations thereof.

As used herein, the term "tissue" refers to biological tissues, generally defined as a collection of interconnected cells that perform a similar function within an organism. Four basic types of tissue are found in the bodies of all animals, including the human body and lower multicellular organisms such as insects, including epithelium, connective tissue, muscle tissue, and nervous tissue, and additional specialized tissue, such as teeth. These tissues make up all the organs, structures and other body contents.

As used herein, the term "bone" refers to the rigid organs that form part of the endoskeleton of vertebrates and function to move, support, and protect the various organs of the body, produce red and white blood cells and store minerals. One of the types of tissues that make up bone is the mineralized osseous tissue, also called bone tissue, which gives it rigidity and honeycomb-like three-dimensional internal structure. Other types of tissue found in bones include marrow, endosteum, and periosteum, nerves, blood vessels and cartilage.

Cartilage is a type of dense connective tissue composed of collagen fibers and/or elastin fibers that can supply smooth surfaces for the movement of articulating bones. Cartilage is found in many places in the body including the joints, the rib cage, the ear, the nose, the bronchial tubes and the intervertebral discs. There are three main types of cartilage: elastic, hyaline, and fibrocartilage.

Accordingly, the term "tissue" as used herein broadly encompasses all biological components including, but not limited to, skin, muscle, nerves, blood, bone, cartilage, teeth, tendons, ligaments, and organs composed of or containing same, as well as derivatives thereof, such as demineralized bone matrix. While the constructs and assemblies of the present invention have particular applicability to bone treatment, the present invention is not limited thereto. Rather, the teachings of the present invention may be applied to other analogous situations, in connection with other tissues and organs.

In the context of the present invention, the term "plug" or "plug material" refers to any solid, semi-solid, or gel material, or combinations thereof, which when implanted in tissue or the bore of a cannulated implant device, such as a bone screw, provides a full or partial hydraulic barrier to flow from one side of the plug along the linear axis of the hole or bore to the other side. Additionally, said plug material can include one or more liquid components. Typical materials are bio-compatible. Typically, in the case of plugs inserted into non-elastic (or less-elastic) implants or tissue, said plug is comprised, at least in part, of elastomeric or otherwise deformable or shapeable materials. Alternatively, the use of a non-deformable plug material combined with a deformable coating, including, but not limited to, an adhesive is contemplated by the present invention. Plugs inserted into more-elastic implants or tissues (i.e., those that are themselves deformable) may be fabricated from either non-deformable or deformable materials or a combination thereof. Illustrative plug materials include, but are not limited to: polymer solids, foams, films and fibers, with particular value in biodegradable polymers, such as polylactic acid (PLA) and Poly-Lactic-Co-Glycolic Acid (PLGA), biological solids, foams and fibers, such as collagen, bone matrix and bone products treated to exhibit properties, such as elastic or other properties, bone putty, gel and cement and the range of calcium based compounds known to those skilled in the art, adipose tissue, other biological tissue, including autogenic and allogenic tendon and ligament tissue. Additionally, the plug can also comprise balloon-type constructs and highly viscous materials. Additional components to imbue specific properties to the plug are also of value, such as, but not limited to the use of fibrin glue and related materials to increase the adhesion between the plug and the wall of the hole in the tissue or bore of the implant device. Bone void fillers, such as collagen mixed with calcium phosphate salt or other calcium molecule bearing compounds, or collagen mixed with demineralized bone matrix are readily available and are of value as plug materials in the context of the present invention. Of particular interest in the context of the present invention are materials and mixtures which expand through absorption of water or other materials, such as mixtures comprising, in part, hydrophilic materials which form hydrogels, or materials, such as sponge-like materials, which are maintained in a compressed state by a material with water soluble bonds are of particular interest. Plug materials which under go a state change through change in temperature, such as a bone wax which can transition from a liquid or semi-liquid state to a more solid state once implanted at body temperature are of value. Plug materials which undergo a reactive or solvent based transition to a more solid state are also of interest, such as epoxies, or other cements known to those skilled in the art. Plug materials which comprise different materials in different areas of the plug are of particular interest in the context of the present invention; a plug wherein the walls of the plug have an effective concentration of material which provides increased friction between the plug and the walls of the hole in the bone or bore of the implant device, such as fibronectin based molecules, is of value; as previously mentioned a core of the plug which is expansive in nature and increases the radial force of plug against wall is of value; a material at the proximal end of the plug which abuts to the distal end of the plug pusher which exhibits a low level of binding between the two, such as fibrous polymer, is of value; and other configurations, which might be envisioned by one skilled in the art to achieve the desired effects described herein.

In the context of the present invention, a flow barrier is anything that restricts or impedes, at least in part, the movement of material from one area to another. Typically this is a result of reduction in the open area available for the flow of material. Accordingly, plug materials can present either a complete barrier to flow, such as with a wax plug which occupies all the cross-sectional space, or a partial barrier to flow, such as might be envisioned with a fibrous filter material. In either context, a substantial reduction in fluid flow across the opening is achieved.

In the context of the present invention, in addition to serving as a proximal flow barrier, the plug of the present invention can also be used to itself deliver, either as a bolus or over an extended period of time, a therapeutic material which is identical to or separate from the therapeutic material which is injected; for example, there might be advantages to the plug containing anti-infectious agents. The therapeutic agents which may be contained (e.g., adsorbed) within and dispensed from, preferably over an extended period of time, the material of the plug are analogous to those which may be injected across the plug, via the hypodermic needle, and include those mentioned above. Specifically preferred examples include, but are not limited to, growth factors and other cytokines, stem and progenitor cells, antibiotics, chemotherapeutics and other cancer drugs, imaging compounds, analgesics, and the like as well as combinations thereof.

In the context of the present invention, the "core device", "flow tube", hypodermic needle or other cannulated fluid delivery tube can comprise any fluid portal which can provide a hydraulic path between the proximal side of the plug and the distal side of the plug. The length and gauge of the needle required will vary with the length of the assembled device, the diameter of the hole being injected into and the propensity of the therapeutic material to plug. Of particular value in the context of the present invention is a hypodermic needle with a luer-lock-type fitting, such as might be found with a spinal needle; this type of needle typically has an extended length which makes it of value in transiting the length of the assembled device. In the context of the present invention, the cannulated flow tube can be of any material which is compatible with being provided in a sterile state and does not adversely react with any other component in the system or the body tissue. Stainless steel is in common use for hypodermic needles and is well-suited to the device of the present invention. Polymer tubes, both rigid and flexible are also of value in the present invention. A collapsible tube which only passes fluid when sufficient pressure is introduced at one end is also of value in the present invention, and it should be noted that in such a case, the tube may not have to be removed from the plug after injection of the therapeutic material. The connection of the needle or tube to the therapeutic fluid reservoir and the fluid reservoir itself can be of any form readily envisioned by one skilled in the art; in the context of the present invention, a syringe with luer-lock-type connection is preferred because of the prevalence of these devices on the market.

The "plunger" or "plug pusher" of the present invention may be fabricated from any material having the requisite structural integrity to transit force applied by the surgeon to insert the plug into the hole or bore and maintain the plug in that position during injection of the therapeutic material. Typically, the proximal end (end away from the patient) will have some form of protuberance to afford the surgeon leverage in pushing the plug into the tissue and holding it there during injection and during the process of extracting the hypodermic needle. In the case of a luer-lock-type or other twist type connect on the needle, the plug pusher may, but is not required to, have a design which restricts the ability of the needle to rotate around the linear axis in relation to the plug pusher. Additionally, the plug pusher may, but is not required to, have a positive restraint to maintain the needle in the plug pusher until the surgeon wishes to remove it; said restraint can consist of a removable clip, or any other restraint as might be envisioned by one skilled in the art. Typically, the shaft of the plug pusher will have some type of indicia or mark(s) along the length of the shaft which are covered up by the plug guide cannula as the plug pusher is pushed into the plug guide to displace the plug into the tissue or implant device. The covering up of this mark (or marks) will provide the surgical personnel with a visible indication of the depth of insertion of the plug.

In the context of the present invention, the plug guide (also referred to herein as a plug guide cannula, channel, tube or sleeve) comprises a tube-like structure which constrains the plug in a configuration compatible with insertion into a void of predetermined diameter, protects the plug prior to insertion, engages with the opening of the hole or bore in a manner which is conducive to the transfer of the plug from the plug guide into the hole, provides a positive stop to insure the relative position of the plug guide and the tissue or the cannulated implant device, provides a limiting stop for the plug pusher. The plug guide cannula may also comprise a specialized distal end to mate with bone or implant device in a specific manner, for example, the exterior wall of the plug guide cannula may have a hexagonal cross-section to mate securely with the head of a hex-drive bone screw. The plug guide cannula may also comprise at the proximal end protuberances to facilitate handling by the surgeon, or to provide a limiting stop in the case where the plug guide is being inserted into a surgical cannula that has been used as a guide for forming a hole in tissue or bone. The plug guide cannula may also have incorporated in the proximal end a positive stop to prohibit the plug guide from being pulled off of the plug pusher; this can be accomplished by tabs on the plug guide which run in a groves along a portion of the length of the plug pusher, or through other means readily envisioned by one skilled in the art. The plug guide cannula can comprise any material or combination of materials that provide the requisite structural integrity and are compatible with other components of the system and medical use. Of particular interest in the context of the present invention are low-friction polymers that can be sterilized, such as certain grades of nylon, which have are slightly elastic such that they provide a tight fit to the plug pusher. In some instances, a straight metallic sleeve or a metallic sleeve with a polymer lining may be preferred over a straight flexible polymer sleeve for structural reasons, particularly when dealing with hole diameters less than 2 millimeters.

In certain instances, it may be advantages to advance the plug through a surgical cannula which is of a size which is compatible with the opening in the tissue. This is often the case when a trocar/cannula combination has been used to create the hole in bone. In this case, the surgical cannula of the trocar/cannula combination may be used as the plug guide cannula. The device of the present invention will include a plug guide cannula, or in this case a "plug holder" which mates with the proximal end of the surgical cannula and permits transfer of the plug to the surgical cannula, such that the plug pusher pushes the plug through the surgical cannula and into the bone or implant device.

The present invention is particularly useful for introducing therapeutic materials into the bore of a surgical implant, such as a bone screw. However, the invention is not limited to osteoimplants. It not only finds utility in connection with other type of implants or prosthetic devices but also finds utility in connection with bones or tissue alone, in the absence of such implants. Accordingly, the device and assembly of the present invention may used to introduce therapeutic materials into voids in tissue or bone through openings that are natural, disease-associated or surgically introduced. For example, the device and assembly of the present invention may used to deliver useful material to areas of necrotic or cancerous bone.

In addition to serving as a means for delivering therapeutic materials, the constructs of the present invention also find utility in the aspiration or removal of material from a hole or void in a tissue or bone, for example, aspirating bone marrow from the hip bone or aspirating excess fluid from an arthritic joint. The constructs of the present invention also have spinal column applications as well as potential utility in connection with soft organs and tissues.

Hereinafter, the present invention is described in more detail by reference to the Figures and Examples. However, the following materials, methods, figures, and examples only illustrate aspects of the invention and are in no way intended to limit the scope of the present invention. For example, while the present invention makes specific reference to orthopedic bone screws, it is readily apparent that the present invention has other applications, such as those mentioned herein. As such, methods and materials similar or equivalent to those described herein can be used in the practice or testing of the present invention.

EXAMPLES

Example 1

Treatment of Chronic Degenerative Insertional Tendiopathy

Surgical treatment is provided for a patient with chronic degenerative insertional tendinopathy with thickening fibrosis and tearing of the Achilles tendon from the calcaneus extending approximately 5-6 cm, who has failed conservative treatment. In surgery, the peritinon is incised, the tendon is debrided and all non-viable tendon is removed, the diseased portion of the calcaneus is resected, and the flexor hallucis longus (FHL) tendon is approached. A section of the FHL tendon is harvested and formed into a 5 mmØ×3 mm plug and inserted and securely packed into a plug guide cannula of the present invention by trained personnel. A 2 mmØ guide wire is driven into the calcaneus at the desired point of reattachment of the tendon. A 5 mmØ cannulated drill is then used over the guide wire to create the attachment tunnel. The free end of the portion of FHL tendon which remains attached to muscle is sutured and passed through the tunnel and appropriately tensioned before a 5.5 mmØ×3 mm PLA/PLGA interference screw is inserted in the tunnel to secure the tendon. A syringe with 4 cc of autologous bone marrow aspirate concentrate is attached by means of a luer-lock fitting to the needle of the device of the present invention, and the syringe is depressed sufficiently to clear the needle of entrapped air. The device is then positioned at the head of the interference screw and the plug and needle assembly is displaced into the screw according to the method of the present invention. The bone marrow aspirate is then injected into the region of the screw at the distal side of the plug. The needle is removed while the plug pusher is held in place, and then the plug pusher and plug guide assembly is removed.

Example 2

Treatment of Osteopenia and Interochanteric Femur Fracture

Surgical treatment is provided for a patient with an osteopenia and intertrochanteric femur fracture. The fracture is reduced and a hip screw and plate device is surgically inserted and affixed using 4.5 mmØ×4 cm cannulated titanium screws. In the process of screw placement, the screws are driven to a point representing 75% of the final insertion depth. At that point, a device of the present invention is utilized in conjunction with the screw. The device comprises, in part, a calcium putty plug, and has attached to the needle, a reservoir of methyl-methacrylate bone cement. The device is abutted to the partially inserted screw; the plug pusher is displaced into the plug guide cannula to a point where the plug and the needle tip are displaced into the target screw. The bone cement is then injected into the screw. The needle is removed, and then the plug pusher is removed. The screw is then driven the remaining portion to full depth and, in this process, the driving bit provides the additional benefit of holding the plug in place in the screw during the process of driving the screw further into the bone.

Example 3

Avascular Necrosis of the Femoral Head

A patient with avascular necrosis of the femoral head prior to the onset of subchondral fracture undergoes a procedure for structural decompression that involves core drilling, flushing of the affected zone with a solution thought to halt osteoclastic breakdown (in cases of suspected infection, an antibiotic treatment may be added or substituted), and then treatment of the area with cellular therapy through the insertion of mesenchymal stem cells (MSC) in a autologous plasma matrix which also contains therapeutic levels of platelet-derived growth factor (PDGF). This is accomplished through the following procedure:

(a) An incision is made to access the trochanteric section of femur.
(b) A 6.5 mmØ outside×60 mm surgical cannula is introduced into the incision and placed on the bone as a guide.
(c) A 5 mm drill is introduced into the cannula and under image guidance the affected area is penetrated by a plurality of holes originating from the single cannula access point using a fanning technique.
(d) A construct of the present invention is introduced into the cannula, the construct comprising:
  i. a plug guide cannula with a 5 mm inside diameter and an outside diameter less than the said surgical cannula, and a straight-wall length of 60 mm with a limiting protrusion on the proximal end to constrain insertion in the surgical cannula beyond 60 mm,
  ii. a 7 mm long plug of collagen sponge (also foam) compressed to 5 mm diameter,
  iii. a plug pusher, 5 mm in diameter and 63 mm straight wall length; the plug pusher has a two 18 gauge needles with flexible shafts mounted within the plug guide cannula and eccentrically on opposite sides of the plug.
(e) The surgical cannula is put at an angle to the surface of the bone, and one of the two needles is slid under imaging system guidance into the drill hole at one extreme of the fan pattern to an extent where it extends into an area of necrosis; the surgical cannula is then reoriented to a different angle such that the second needle can be slid under imaging system guidance into a hole at the other extreme of the fan pattern.
(f) The plug pusher is displaced into the plug guide cannula in a manner where the plug enters and seals the drilled entrance hole in the bone which is the focal point of the fan pattern of drill holes.
(g) One needle is attached to a reservoir of an osteoclastic breakdown inhibitor solution and the second to a drain reservoir, and 1 cc/sec of solution is pumped through the area of necrosis for a 10 minute period.
(h) The inhibitor (or alternatively, antimicrobial) solution reservoir is disconnected and the MSC/PDGF solution is then introduced into the same needle until either the supply of MSC/PDGF solution is exhausted or there is evidence of the same in the needle to the drain.
(i) The needles are removed from the plug pusher/plug guide cannula assembly, and then the assembly is removed from the surgical cannula.

INDUSTRIAL APPLICABILITY

The present invention provides a means for introducing and retaining a broad range of therapeutic cells, particularly stem cells, and other biologically significant and/or bioactive molecules in cannulated implants as well as in surgical holes in bone, cartilage, teeth and other tissue. Applicable procedures that would benefit from the devices and assemblies of the present invention are common in orthopedic surgery, including spinal surgery, and dentistry. The present invention provides the surgeon with tools and devices which are compatible with existing surgical techniques and permits a more focused delivery of often expensive therapeutic materials. The present invention has particular value in the introduction of stem and other precursor cells, bioactive cytokines, including but not limited to growth factors as well as to the introduction of anti-cancer drugs, particularly those having a toxic effect and for which restricted application is desired.

The devices, constructs, assemblies and methods presented herein provide for increased efficiency of operation in a surgical operating room environment with reduced potential for error. The devices, constructs, assemblies and methods also may result in fewer avenues of potential bacterial infections during surgeries. The efficiencies derived from the methods of the present invention can reduce the time in surgery, which, in turn, can reduce the stress on the patient's body and has the potential to reduce the cost of the surgical procedure. The ability to efficiently introduce and retain therapeutic materials may result in a faster recovery from a medical condition.

The disclosure of each publication, patent or patent application mentioned in this specification is specifically incorporated by reference herein in its entirety. However, nothing herein is to be construed as an admission that the invention is not entitled to antedate such disclosure by virtue of prior invention.

While the invention is herein described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention, the metes and bounds of which are defined by the appended claims.

What is claimed:

1. An assembly for delivering therapeutic material into a void in a tissue or implanted prosthetic device, said void accessed by means of a proximal opening, said assembly comprising:
   a. a plug having distal and proximal ends and a linear axis extending therebetween;
   b. one or more fluid cannulated flow tubes penetrating said plug proximal end, extending through its axial dimension and penetrating said plug distal end to thereby establish a fluid channel across said plug;

c. a plug delivery structure comprising:
   i. a plug guide cannula having open proximal and distal ends and an axial bore extending therebetween, said bore housing said plug and one or more fluid cannulated flow tubes, constraining said plug in a radial direction, and serving as a channel for guiding said plug and cannulated flow tubes into said void;
   ii. a plug pusher that transmits an axial displacement force to the proximal end of said plug to dislodge said plug from said plug guide cannula into said void, wherein said plug, no longer constrained by said plug guide cannula, engages the proximal opening of said void to provide a full or partial hydraulic barrier that impedes flow from the distal side of said plug, out of said void via said proximal opening, and
   iii. a mechanism that coordinates the distalward axial displacement of said plug simultaneous with the distalward axial displacement of said one or more cannulated flow tubes into said void.

2. The assembly of claim 1, wherein at least one of said one or more fluid cannulated flow tubes comprise a hypodermic needle.

3. The assembly of claim 1, wherein said one or more fluid cannulated flow tubes are concentrically disposed within said plug.

4. The assembly of claim 1, wherein said one or more fluid cannulated flow tubes are eccentrically disposed within said plug.

5. The assembly of claim 1, wherein at least one of said one or more fluid cannulated flow tubes comprises a collapsible tube that, in the absence of proximal fluid pressure, provides a full or partial hydraulic barrier impeding flow through the cannulated flow tube from the distal side to the proximal side of said plug.

6. The assembly of claim 1, wherein said plug is fabricated from a biocompatible, solid, semi-solid, matrix, foam, gel, hydrogel or fibrous material.

7. The assembly of claim 6, wherein said plug is comprised, at least in part, of collagen.

8. The assembly of claim 6, wherein said plug is comprised, at least in part, of calcium molecules.

9. The assembly of claim 6, wherein said plug is comprised, at least in part, of a bone product selected from the group consisting of bone, bone matrix, bone putty, bone gel and combinations thereof.

10. The assembly of claim 6, wherein said plug is comprised, at least in part, of a bone cement, bone wax, sealant or adhesive or a combination thereof.

11. The assembly of claim 6, wherein said plug is comprised, at least in part, of a biodegradable polymer foam, sponge, hydrogel or fiber.

12. The assembly of claim 6, wherein said plug is comprised, at least in part, of a polymer selected from the group consisting of polylactic acid (PLA), Poly-Lactic-Co-Glycolic Acid (PLGA), and combinations thereof.

13. The assembly of claim 6, wherein said plug is comprised, at least in part, of a biological tissue.

14. The assembly of claim 6, wherein said plug is comprised, at least in part, of material selected from the group consisting of bone marrow, adipose tissue, tendon and ligament tissue, and extracts or combinations thereof.

15. The assembly of claim 1, wherein said plug houses one or more therapeutic materials.

16. The assembly of claim 15, wherein the one or more therapeutic materials is selected from the group consisting of stem cells, progenitor cells, biological cells, BMP, PDGF, TGF, growth factors, antimicrobials, clotting agents, fibronectin, and anticoagulants.

17. The assembly of claim 15, wherein said therapeutic materials are released from said plug upon insertion into said void, either immediately or over time.

18. The assembly of claim 15, wherein said therapeutic materials are not released from said plug upon insertion into said void.

19. The assembly of claim 1, wherein said plug expands through the absorption of liquid to impede flow of fluid out of said void via said proximal opening after said one or more fluid cannulated flow tubes are partially or completely removed.

20. The assembly of claim 1, wherein said plug is provided with an adhesive coating to facilitate bonding between said plug and the walls of said void.

21. The assembly of claim 1, wherein said plug pusher comprises an elongated shaft having a plunger component at its distal end.

22. The assembly of claim 1, wherein the axial bore of said plug guide cannula has an inside diameter at its distal end that is approximately equal to or less than the inside diameter of said proximal opening of the void such that said plug can be pushed from the plug guide and into the void with minimal disruption of the plug.

23. The assembly of claim 1, wherein the axial bore of said plug guide cannula is provided with decreasing cross-sectional area, tapering towards its distal end, such that the plug is compressed just prior to the plug being introduced into the void.

24. The assembly of claim 1, wherein the axial bore of said plug guide cannula has an inside diameter at its distal end that is greater than the inside diameter of the proximal opening of the void and the plug is of a configuration wherein the distal end of said plug has a diameter less than the inside diameter of the proximal opening of the void and the proximal end of said plug is greater than the proximal opening of the void.

25. The assembly of claim 1, wherein the plug guide cannula mates with a surgical cannula acting as an extension to the plug guide cannula, wherein the plug is transferred through the surgical cannula and into the proximal opening of the tissue void.

26. The assembly of claim 1, wherein distal end of said plug guide cannula is provided with a hex configuration that is compatible with the hex driver head conventional in the art of bone screws.

27. The assembly of claim 1, wherein said plug delivery structure is provided with visual indicia of the depth to which the plug has been inserted into the void.

28. The assembly of claim 27, wherein said visual indicia comprise one or more axially spaced markings along the lengths of the plug guide cannula and/or plug pusher.

29. The assembly of claim 1, wherein the relative linear dimensions of the one or more cannulated flow tubes, the plug guide cannula, plug and the plug pusher are such that when used together,
   (a) the distal end of the one or more cannulated flow tubes is deployed at a predetermined depth into said tissue or implanted prosthetic device,
   (b) the plug is inserted at a predetermined depth, and
   (c) the relationship of the distal end of the one or more cannulated flow tubes and the distal end of the plug are predetermined and allow for free passage of therapeutic material to the distal side of the plug.

30. The assembly of claim 29, wherein said prosthetic implant device is a bone screw.

31. The assembly of claim 1, wherein the components (a) - (c) are packaged together in a sterile and assembled state.

32. The assembly of claim 1, wherein one or more of the components (a) - (c) are separately packaged in a sterile yet unassembled state.

33. The assembly of claim 1 wherein the proximal ends of said one or more cannulated flow tubes are attached to one or more fluid reservoirs.

34. The assembly of claim 33, wherein said one or more fluid reservoirs contains therapeutic molecules.

35. The assembly of claim 33, wherein said one or more fluid reservoirs contains stem cells or other biological cells.

36. The assembly of claim 33, wherein said one or more fluid reservoirs contains material selected from the group consisting of bone marrow products, blood products, adiposes tissue products, and fluids from the reproduction system or products thereof.

37. The assembly, of claim 33, wherein said one or more fluid reservoirs contain cements, adhesives, fillers or tissue scaffold materials.

38. The assembly of claim 33, wherein said one or more fluid reservoirs contains a flush media.

39. The assembly of claim 1, wherein said mechanism for coordinating simultaneous distalward axial displacement of said plug and one or more flow tubes comprises a force transmitting contact or linkage between one of said cannulated flow tubes and said plug pusher.

40. The assembly of claim 1, wherein said mechanism for coordinating simultaneous axial displacement of said plug and one or more flow tubes comprises a linkage between one of said cannulated flow tubes and said plug pusher.

41. The assembly of claim 40, wherein said locking linkage comprises interlocking luer tapers.

42. The assembly of claim 40, wherein said linkage comprises a locked configuration, wherein said flow tube and plug pusher move as a single unit, and an unlocked configuration, wherein the plug pusher maintains the plug in position while said flow tube is retracted.

43. The assembly of claim 40, wherein said linkage comprises a removable stop pin or clip that temporarily secures one of said cannulated flow tubes to said plug pusher so as to ensure coordinated axial movement of the two.

44. A method for delivering therapeutic material into a void in a tissue or implanted prosthetic device, said void accessed by means of a proximal opening, using the assembly of claim 1, said method comprising the steps of:
   a. inserting said one or more fluid cannulated flow tubes through said plug to form a unitary component;
   b. introducing said unitary component into the axial bore of said plug guide cannula;
   c. displacing said unitary component from said axial bore into said void by means of said plug pusher, wherein said plug provides at least a partial hydraulic barrier in said proximal opening to impede fluid outflow therethrough;
   d. injecting one or more therapeutic materials through said one or more fluid cannulated flow tubes, into the void on the distal side of the plug; and optionally
   e. removing said fluid cannulated flow tubes in a manner whereby the plug and therapeutic material remain in the tissue or implant device.

45. The method of claim 44, wherein said step (d) involves attaching a syringe or other reservoir containing one or more therapeutic materials to the proximal end of said one or more fluid cannulated flow tubes.

46. A method for removal of material from a void in a tissue or implanted prosthetic device, said void accessed by means of a proximal opening, using the assembly of claim 1, said method comprising the steps of:
   a. inserting said one or more tubes through said plug to form a unitary component;
   b. introducing said unitary component into the axial bore of said plug guide cannula;
   c. displacing said unitary component from said axial bore into said void by means of said plug pusher, wherein said plug provides at least a partial barrier in said proximal opening;
   d. aspirating or otherwise removing materials through said one or more tubes, from the void on the distal side of the plug; and optionally
   e. removing said tubes in a manner whereby the plug remains in the tissue or implant device.

\* \* \* \* \*